(12) United States Patent
Slocum et al.

(10) Patent No.: US 6,430,306 B2
(45) Date of Patent: *Aug. 6, 2002

(54) SYSTEMS AND METHODS FOR IDENTIFYING IMAGES

(75) Inventors: Lee G. Slocum, Amherst, NH (US); Yona Weider, Newton, MA (US)

(73) Assignee: LAU Technologies, Acton, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/879,471

(22) Filed: Jun. 20, 1997

Related U.S. Application Data

(63) Continuation of application No. 08/408,517, filed on Mar. 20, 1995, now abandoned.

(51) Int. Cl.[7] .................................................. G06K 9/00
(52) U.S. Cl. ....................................................... 382/118
(58) Field of Search ................................. 382/115, 117, 382/118, 116, 190, 305–306; 380/23; 283/75, 77; 235/380

(56) References Cited

U.S. PATENT DOCUMENTS

| | | | | |
|---|---|---|---|---|
| 4,827,522 A | * | 5/1989 | Matsuura et al. ........... | 381/143 |
| 4,993,068 A | | 2/1991 | Piosenka et al. ............. | 380/23 |
| 5,164,992 A | | 11/1992 | Turk et al. .................. | 382/118 |
| 5,432,864 A | * | 7/1995 | Lu et al. ...................... | 382/118 |
| 5,469,512 A | * | 11/1995 | Fujita et al. ................. | 382/118 |
| 5,505,494 A | | 4/1996 | Belluci et al. ................ | 283/75 |
| 5,550,928 A | * | 8/1996 | Lu et al. ..................... | 382/116 |

OTHER PUBLICATIONS

Murase et al., "Visual Learning and Recognition of 3–D objects from Appearance", Department Computer Science, Columbia University, pp. 1–31 (1993).*
Pentland et al., "View–Based and Modular Eigenspaces for Face Recognition", *IEEE, Conference on Computer Vision & Pattern Recognition,* No. 245, pp 1–7 (1994).
Turk et al, "Eigenfaces for Recognition", *Journal of Cognitive Neuroscience,* vol. 3, No. 1, pp. 71–86 (1991).
DeJesus, "Faster and More Sophisticated Algorithms are Helping Computerized Facial–Recognition Systems Come of Age", *State of the Art, Face Value,* pp. 85–90 (1995).

* cited by examiner

*Primary Examiner*—Jayanti K. Patel
(74) *Attorney, Agent, or Firm*—Lahive & Cockfield, LLP

(57) ABSTRACT

Systems and methods are disclosed that employ facial recognition to create, maintain and use databases that store data records of individuals. In particular, systems and methods are disclosed that employ facial recognition to control the production of identification cards that include an image of a person's face and demographic data. Preferably, the systems and methods include lensing modules adapted for efficiently identifying within a picture image the location of a person's face.

12 Claims, 3 Drawing Sheets

US 6,430,306 B2

SYSTEMS AND METHODS FOR IDENTIFYING IMAGES

This application is a continuation of application Ser. No. 08/408,517 filed on Mar. 20 1995 now abandoned.

FIELD OF THE INVENTION

The field of the invention relates to systems and methods for data processing and more particularly to systems and methods that employ facial recognition to manage databases containing images of individuals.

BACKGROUND OF THE INVENTION

Computerized databases can be adapted to store many different kinds of data, including sounds, images and text. This flexibility allows database designers to construct databases that have data records that organize and store information in several different formats, such as text and sound and thereby to provide database systems that are more particularly suited to the application at hand.

In one common example, government agencies and businesses use computer databases to store information about select individuals into data records that include demographic data stored as text information and a picture of the individual stored as a digitally encoded image. Therefore, a State Department of Motor Vehicles, can create a database of registered drivers that includes a data record for each registered driver. Each data record can store text information, such as the driver's name and address, and image information, such as a digitally encoded picture of the driver. The Department of Motor Vehicles can maintain this record, and continually update the contents as the driver's history and data change.

Although computer databases provide an efficient way to store image and text data, they generally fail to provide any way to search or sort the image information stored therein. This inability is particularly burdensome if the image information is the most reliable or complete information in the data record.

Moreover, this inability prevents an operator from automatically searching through the database to find a particular image of a person. Accordingly, to search the images in a database, the operator must call up each data record and view that record's stored image. This is such a time consuming and labor intensive process, that image searches of large databases is practically impossible. Consequently, there is little to prevent a person from registering multiple times with an agency, such as the Registry of Motor Vehicles, or a State Welfare Department, by providing fraudulent demographic data during each registration.

Moreover, the quality and characteristics of the images stored in the database can vary widely. For example, the grey scale of any two images can be markedly different. These variations make it more difficult for an operator to compare stored images.

Therefore it is an object of the present invention to provide improved systems and methods for maintaining databases that store image information as part of a data record.

It is a further object of the present invention to provide systems and methods that can efficiently employ image information to control the entry of data into a database.

It is yet another object of the invention to provide improved systems and methods for storing image information in a normalized format within a database.

These and other objects of the present invention will become apparent by following the description of certain embodiments of the present invention.

SUMMARY OF THE INVENTION

The present invention provides systems and methods that employ facial recognition to create, maintain and use databases that store data records of individuals. In particular, the present invention provides systems and methods that are adapted to employ select facial recognition techniques to analyze a picture of a person's face. These select facial recognition techniques generate a set of values, hereinafter referred to as a "projection signal", that, as a set, are descriptive of the analyzed picture image and provide for highly compact storage of the critical identity characteristics of a person's face. The generated projection signal can be stored as a data field in a data record that is associated with the individual depicted in the picture. This data record can also include demographic data fields for organizing information, such as address information, social security numbers, and other identifying information with the image information. The invention provides systems and methods that are adapted to work with data records that include data fields of descriptive image information, and to provide systems that can search, compare and sort data records according to image information recorded therein.

To this end, systems and methods are described for creating and employing databases that have data records which contain image information of a person's face. These database systems and methods are adapted for efficiently storing, sorting, and comparing data records as a function of the image of a person's face.

In one embodiment of the invention, systems are provided for manufacturing identification cards, such as driver's licenses, military identification cards, welfare identification cards, pistol permits and other photo-identification cards. The systems are adapted for performing a select principal component analysis facial recognition technique. The facial recognition technique employed by the present invention allows, in one use, the systems to police the manufacture of identification cards to eliminate issuing multiple cards under different names to a single applicant.

These systems generally include an image acquisition element, such as a video camera or a photographic camera and a scanner, that generates a digitized picture of the applicant's face. A vector memory stores a plurality of eigenvectors defining a multi-dimensional image space. A data processor, such as a conventional workstation, is configured to project the digitized picture onto the multi-dimensional image space, to encode the picture as a weighted function of the plural eigenvectors. An image database couples to the data processor to provide storage for a database of known projection signals each being representative of a weighted set of the eigenvectors associated with an image of a specific person's face. A demographic database stores a number of data records wherein each data record is associated with a respective one of the stored projection signals and the individual whose image is represented thereby. Each data record also includes an identification signal for identifying that particular data record.

Typically, the data processor includes a recognition program element that is adapted for recognizing a person. Generally, the recognition program element compares the generated projection signal against the projection signals stored in the system. As the projection signals represent the image of a person's face, similar projection signals are likely to represent the same person or a person with a similar appearance. Therefore, the program element is adapted to determine whether the generated projection signal is substantially representative of one or more of the stored projection signals and to indicate if a match is detected.

In a further embodiment, the recognition program element includes a text query element for comparing text information with the identification signals stored in the data records. The text query element compares, sorts and orders data records as a function of text signals, such as demographic data, stored in the data records. In an optional configuration, the recognition program element employs the text query element to identify a subset of data records as a function of select demographic data. In a subsequent operation, the recognition program element operates on the subset of data records to determine whether the generated projection signal is substantially representative of one of the stored projection signals.

In a preferred embodiment of the present invention, these systems include a location device that searches through the acquired picture to identify a portion of the picture that contains an image of a person's face. For example, in a picture that depicts a person standing in front of a wall in a police line up, the location device will ignore the background wall and other clutter and will identify that portion of the picture that contains the image of the person's face. In one embodiment, the location device has a prefilter element that makes a preliminary examination of one portion of the picture to determine if that portion of the picture is likely to contain the image of a person's face. One type of prefilter element has a grey-scale variance detector that determines how much variance exists between the grey-scale of the selected picture portion, and the typical grey-scale of a picture portion that contains a face. This computationally efficient calculation allows the prefilter element to distinguish quickly between a portion of the picture that depicts a wall or a screen positioned behind the person, and a portion of the picture that contains the image of the person's face.

Preferably the recognition program element also includes a normalizing element that adjusts the acquired picture according to preselected user criterion. The normalizing element typically includes an element for selectively adjusting a grey-scale parameter of the acquired picture, and an element for selectively adjusting an inclination or tilt parameter of the picture. This normalization element helps minimize problems during the recognition process which are caused by variations in conditions, such as lighting, during image acquisition.

In one embodiment, an enforcement mechanism monitors the recognition program and notes if any matches occur between the generated projection signal and the stored projection signals. The enforcement mechanism notes each favorable comparison and makes a list of every data record that appears to contain an image of the person applying for an identification card. The enforcement mechanism may further include an image server element that is adapted for storing pictures associated with respective ones of said data records. A monitor coupled to the image server displays the pictures of those people that have similar image characteristic as the applicants. An operator can detect if the Applicant is attempting to register into the database under a different name.

In another option, a printer element can connect to the system and record information representative of the picture signal and the identification signal onto a blank data card to generate an identification card. In one embodiment, the enforcement mechanism couples to the printer and prevents the printer from printing an identification card for any data record associated with a picture that is substantially similar to the picture of the applicant.

In a further embodiment of the present invention, the identification card manufacturing system also includes a selection element that selects a portion of the picture that represents a select characteristic of the applicant's face. In one example, the selection element selects the portion of the picture that represents the applicant's eyes. By analyzing one portion of a person's face, the system can recognize a person that is wearing a disguise, such as a beard or wig. In this example, the system projects the portion of the picture that includes the image of the person's eyes onto the multi-dimensional space, and generates a set of values that are descriptive of this portion of the picture. The recognition program element compares the generated values against values stored in the database and identifies data records having images similar to the applicant's image.

In another embodiment of the present invention, systems are provided for sorting pictures stored with data records. In particular, systems are described that sort pictures as a function of the class of object, such as whether the image can be classified as a face, an eye, or a mouth. These sorting systems are adapted for sorting through a database of pictures to identify those pictures that represent a select class of objects. In one particular example, the sorting system is adapted to sort through a database of pictures to identify those pictures that represent the face of a person. The system can then make a list of the data records that fail to contain an image of a face, and a system operator can examine these records to identify those records that are to be deleted from the system.

Generally these systems include a picture memory adapted for storing picture signals, a reference memory having storage for the plural eigenvectors of a multi-dimensional image space and having storage for a subspace signal representative of a subspace defined by the plural eigenvectors, a selection element for selecting a picture signal from the picture memory and for generating a projection signal representative of the picture signal encoded as a weighted function of the plural eigenvector signals, a computing element for computing a distance signal that represents the distance between a point defined by the projection signal and the space defined by the subspace signal, and a classification element for determining as a function of the distance signal whether a picture signal is representative of an image of a person. This system therefore provides a mechanism to search through a database of images and identify those data records that contain image data of a particular class of objects, such as faces.

In one embodiment, these systems include an element for deleting automatically a picture signal from the picture memory as a function of the distance signal. Optionally, the system includes a demographic database memory for storing data records, and an element for deleting a data record from the demographic database as a function of the generated distance signal.

The invention will now be explained with reference to certain illustrated embodiments to provide greater detail of the structure and operation of the systems and methods that can be realized by the present invention.

BRIEF DESCRIPTION OF THE ILLUSTRATED EMBODIMENTS

DETAILED DESCRIPTION OF THE ILLUSTRATED EMBODIMENTS

Figure 1:
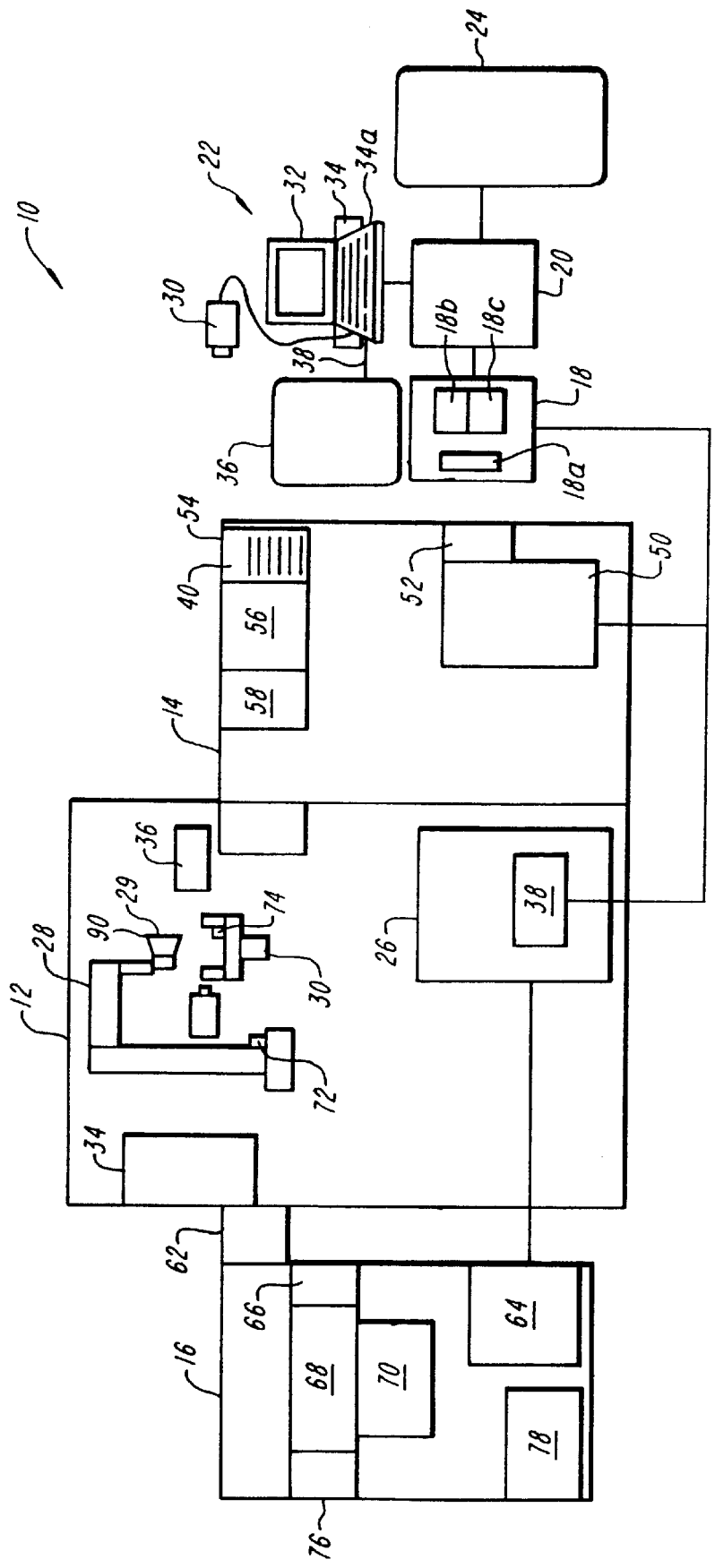
FIG. 1 illustrates a system for manufacturing identification cards which includes a data acquisition element that employs facial recognition to control data records entered into a database.

FIG. 1 illustrates a system 10 for manufacturing identification cards, such as driver's licenses, welfare cards, firearm identification cards, military identification cards and other identification cards that typically reproduce in a printed format demographic data and an image of an individual. The image and demographic data recorded onto an identification card is generally reliable, as identification cards typically include seals, signatures and other devices that make forgeries difficult to produce. Accordingly, businesses and government agencies commonly provide identification cards to those individuals that are registered, into an official record maintained by the agency. Typically, these official records are maintained in a computer database that includes a data record, or file, for each registered individual. The system 10 illustrated in FIG. 1 is adapted to control such an official record by controlling the data entered into the official record and by accessing information in these records to manufacture identification cards.

To this end, the system 10 is adapted to analyze data records being stored in a database of official records and to control the manufacture of identification cards that represent in recorded form, information from a data portion of an official record. The system 10 includes a vision inspection cell 12, a recording unit 14, a packaging unit 16, a network job builder unit 18, a central image server 20, a data acquisition unit 22, and a demographic database memory 24. System 10 illustrated in FIG. 1 is one system constructed according to the invention, that employs facial recognition techniques to manage and control a database containing image information that includes at least in part, images representative of a person's face. In particular, the system 10 employs facial recognition technology to prevent a single individual from acquiring multiple identification cards, such a drivers licenses, under different names. Additionally, the system 10 can sort a database of images to remove from the database those data records that contain insufficient or incorrect image information, and can process and adjust image information to generate an image signal suitable for printing on an identification card.

The illustrated system 10 includes a recording unit 14, vision inspection cell 12 and packaging unit 16 that generate and inspect identification cards. Such units are described in U.S. patent application Ser. No. 08/316,041, entitled "Systems and Methods for Recording Data", filed Sep. 30, 1994, assigned to the Assignee hereof, and incorporated herein by reference. The data acquisition element 22 acquires information necessary to generate an identification card. The data acquisition element 22 can examine and process an acquired image to detect if this image is substantially similar to an image already recorded into the database. Additionally, the data acquisition element 22 can process the required image to determine if it is likely to represent the image of a person's face. Once the information is analyzed, the data acquisition element 22 determines if the acquired information is to be entered as a data record in the official register database. The data acquisition element 22 transmits acquired images to the control image server 20 data memory. The central image server 20 data memory acts as a depository for images collected by the data acquisition element 22. Optionally, the system 10 includes a separate database memory, such as the database memory 36, which stores the images acquired by the data acquisition element 22.

The central image server 20 can access demographic data from the demographic database 24 and send image and demographic information to the network job builder unit 18. The network job builder unit 18 collects the image and demographic data together and issues a command to the recording unit 14, that requests the recording unit 14 to record information onto a datacard 40. The recorded information includes the image acquired by the data acquisition element 22 and demographic data acquired from the demographic database memory 24. The recording unit 14 passes the recorded data card to the vision inspection cell 12. The vision inspection cell 12 inspects the information recorded onto the datacard 40 to determine if the recorded datacard meets certain user selected criteria. The inspection cell 12 passes the inspected datacard to the optional packaging unit 16.

The packaging unit 16 receives a signal from the vision inspection cell 12 that indicates whether or not the recorded datacard 40 has been successfully manufactured. If the card has been successfully manufactured, the packaging unit 16 places the recorded datacard 40 into a carrier element, such as an envelope, and prepares the envelope for distribution, typically by mail. Alternatively, if the vision inspection cell 12 indicates that the recorded datacard 40 fails to meet user selected criteria, the packaging unit 16 places the recorded datacard 40 into a disposal bin.

With reference again to FIG. 1, the data acquisition element 22 can be described in more detail. The illustrated data acquisition element 22 is a programmable hardware device that includes an image acquisition element 30, a monitor 32, a data processor 34, a keyboard 34A, and an optional image database memory 36. As further illustrated by FIG. 1, the data processor 34 connects via transmission paths to the image database memory 36 and to the central image server 20. The data processor 34 further connects via a transmission path to the image acquisition element 30, that is depicted in FIG. 1 as a camera, such as a video camera that acquires images and generates standard video signals representative of the acquired images. The illustrated data processor 34 is a conventional computing system, such as a SUN SPARK workstation, that includes a video interface card for interfacing with the camera acquisition element 30. The data processor 34 further includes a program element, i.e., an application program, that controls these elements to acquire, process and store both image and text information.

The image acquisition element 30 which can be a camera, such as a video camera, that captures image data that is representable by pixel data. The depicted image acquisition element 30 is a video camera that produces an analog video signal that encodes an image as pixel data. The video signal can be formatted into any of the conventional video formats, including RS-170/CCIR or any proprietary video format. The analog signal is received by a camera interface in the data processor 34. Alternatively, the image acquisition element can be a digital camera that generates image information in a digital format. Other image acquisition elements can be practiced with the present invention without departing from the scope thereof.

In an alternative embodiment, the image acquisition element 30 is a scanner element that is adapted for scanning photographic film pictures into a computer memory. One such scanner is the AVR3000 manufactured by AVR Technology of San Jose, Calif. The scanner element image acquisition unit encodes the photographic film picture into pixel data and transmits the pixel data to the data processor 34 to thereby provide the data processor 34 with a machine readable representation of a picture. Other image acquisition elements suitable for representing an image or picture in machine readable form are practicable with the invention without departing from the scope of thereof.

The illustrated optional monitor 22 is a conventional video display monitor such as the type commonly employed for displaying video images including text, graphics, and images. As will be explained in greater detail hereinafter, the data processor 34, in one embodiment, operates the video monitor 32 to display picture signals representative of images of individuals which are maintained as image files within the image database 36.

The database memory element 36 stores data records, or electrical signals representative of data records, wherein each data record is associated with an individual that has been registered into the database. The database memory 36 can be any conventional addressable computer memory adapted for storing electrical signals representative of data, and can include electrical circuit card assemblies adapted for storing information and/or controlling data storage devices, such as optical storage disks, hard disks, and tape drives. The database stored in memory element 36 can be a database of all registered drivers within a certain state, all individuals registered into a state welfare program, all individuals in a state that have been issued firearm identification cards, and so forth. Each data record stored within the memory element 36 can be employed by the system 10 to generate an identification card. The identification card can be issued to a qualified individual to verify that particular individual has been validly registered with an authorized agency or entity and has been granted the privileges identified by the issued identification card. As can be seen from this description, it is a function of the system 10 to maintain the integrity of the database stored in the database memory 36. In particular, it is a function of the system 10 to prevent an individual from fraudulently obtaining one or more identification cards under different names.

The illustrated demographic database memory 24 is a conventional computer memory of the type commonly used for storing data, or electrical signals representative of data, for use by a data processing unit such as the data processing unit 34. The demographic database memory 24 stores data records representative of individuals whom have been registered by an agency into an official record. Accordingly, the database stored in the demographic database memory 24 represents the official record of those individuals that are officially registered as authorized users, members, or participants in a program or other organization administered by an agency such as a business or government agency.

The data processor 34 depicted in FIG. 1, is a data processor having a processing unit, data memory, and program memory. Additionally, the depicted data processor 34 includes a video interface card of the type suitable for interfacing with a camera element that generates electrical signals representative of video images. In one embodiment, the data processor 34 is a SUN workstation, however it should be apparent to one of ordinary skill in the art that other data processor systems are employable with the present invention without departing from the scope thereof. The data processor 34 includes a data record verification module that analyzes information acquired by the data acquisition element 22 and determines if the acquired information is to be entered as a data record into the official record maintained within the demographic database 24. In a preferred embodiment of this invention, the verification module is implemented as a program element stored in the program memory of the data processor 34, however it should be apparent to one of ordinary skill in the art of electrical engineering that the verification module can also be implemented as an electrical circuit card assembly.

Figure 2:
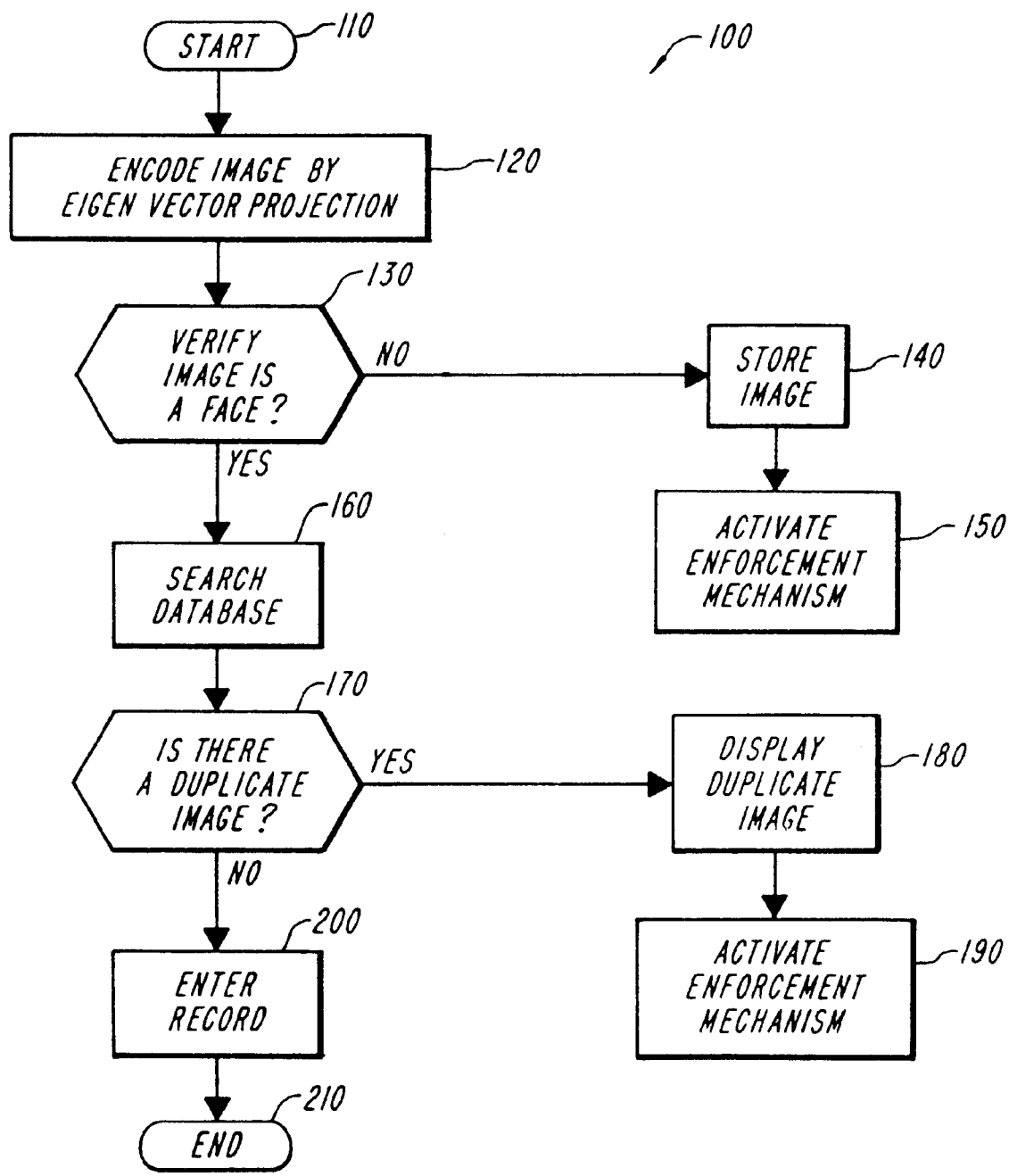
FIG. 2 is a flow chart diagram of a process for verifying information stored in a data record.

FIG. 2 illustrates a flow chart diagram of a process 100 performed by the verification module. The process 100 employs image information acquired by the acquisition element 30 and text information entered at the keyboard element 34A to verify each data record being entered into the official database stored in the database memory 24. The process 100 begins at step 110 when the data acquisition element 22 has acquired sufficient information to generate a data record. For example, the data acquisition element 22 depicted in FIG. 1 collects information for a data record that includes an image of an applicant for a driver's license and the necessary descriptive demographic information. In step 120 the process 110 encodes the image information acquired by the image acquisition element 30. The encoding process includes an eigenvector projection technique that encodes an image of a person's face as a weighted set of eigenvectors.

This eigenvector projection technique is described more fully in U.S. Pat. No. 5,164,992, entitled "Face Recognition System", issued to Turk et al., and incorporated by reference herein. As described therein, an image of a face is projected onto a space defined by a set of reference eigenvectors. The reference set of eigenvectors, or eigenfaces, can be thought of as a set of features which together characterize the variation between face images within a reference set of face images. This distribution of faces in the reference set of faces can be characterized by using principal component analysis. The resulting eigenvectors define the variation between the face images within the reference set of faces, and can be referred to as eigenfaces.

In one embodiment of the invention, a training reference set of faces is produced by acquiring a number of pictures, e.g. 60 pictures or more for obtaining 40 eigenfaces. The training set is normalized so that all faces are the same scale, position, orientation, mean, and variance. Face images are read in from a database. The location of the eyes is identified. In one practice, an operator uses a mouse to locate manually the eyes in the image of the face. The face images are converted to gray scale, normalized, and stored as raw images (as opposed to BMP, or JPEG or other format). The composition of the training set preferably includes examples of types of people expected when the system is eventually used. For example, men and women, whites, blacks, people with glasses, people without glasses, people with beards, people with mustaches, etc. The face images are converted from eight bit gray scale to floating point format. The mean is found by adding all the faces together in the training set and then dividing by the number of face images. The mean is subtracted from all the face images. A matrix is formed from the resultant mean adjusted faces. For example, assume the original face images were 128 pixels by 128 pixels. An entire face image would take up 16384 pixels. Assume this is a column in a matrix of floating point numbers. Other faces in the training set make up the other columns in the matrix. The covariance matrix is computed and the eigenvectors are determined by solving the Jacobian matrix.

The eigenvectors can be sorted from large to small and the most significant eigenvectors are picked according to how many vectors are wanted, e.g. pick 40 out of 60 if the training set was 60. Using the eigenvectors and the training set, the system computes the principal components of the original matrix. These are the "eigenfaces." For example, the system can pick the first eigenvector which is a vector with 60 elements. An eigenface is formed by multiplying each face in the training set by the corresponding coefficient in the eigenvector. Once the eigenfaces are identified an image signal can be represented as a function of these eigenfaces by projecting the image signal into the space defined by these eigenfaces.

The projected face image represents a point within this space. In step 130, the verification module verifies that the image acquired by the image acquisition element 30 is an image of a face by computing the distance between the point in the space which defines the acquired image and a portion of the space, a subspace, that generally indicates that portion of the space onto which an image of a face maps. In other words, the reference set of eigenvectors defines an image space into which images captured by the image acquisition element 30 are mapped. Similar images generally have similar features and therefore, have similar coordinates within this image space. Accordingly, similar images, such as images of people's faces, generally map closely together within a particular portion of the image space. This defines a subspace within the image space which is likely to contain similar types of images. Accordingly, if the point defined by the projected image is sufficiently distant from the subspace that generally defines the portion of space where faces generally map onto, then the verification module determines that the image acquired by the image acquisition element 30 fails to represent an image of a person's face. Alternatively, if the point that defines the acquired image is sufficiently close to, or maps into, the subspace that generally defines the location of faces, the verification module verifies that the acquired image represents an image of a person's face.

If the verification module, in step 130, verifies that the acquired image fails to contain, or represent, an image of a person's face, the process 100 proceeds to step 140. In step 140 the verification module stores the image acquired by the image acquisition element 30 in a buffer for later use. The verification module then proceeds to step 150 and activates an enforcement mechanism which prevents a data record that includes the acquired image from being generated and entered into the official database.

Alternatively, if the verification module in step 130 verifies that the acquired image includes, or represents, the image of a person's face, the process proceeds to step 160.

In step 160, the verification module employs the projection signal, i.e. the image signal encoded as a weighted set of eigenvectors, or eigenfaces, to search the official record database to identify any records having a projection signal, i.e. a weighted set of eigenvectors, similar to the projection signal of the acquired image. Similar weighting coefficients indicate similar images. If the verification module in step 170, determines that there is one or more very similar or duplicate images existing within the official record database 24, the process proceeds to step 180, and displays these duplicate images, and then proceeds to step 190 and activates the enforcement mechanism.

Alternatively if the verification module, in step 170, determines that there is no duplicate image within the record database 24, the verification module verifies that the data record is to be entered into the database memory 24. In step 200 the verification module enters the data record within the database memory element 24. Once the data record is entered, the verification module proceeds to step 210 and ends the process.

In one embodiment of the present invention, the enforcement mechanism includes a display module, that can be an application program element within the data processor 34, that displays to the monitor 32 each image within the database stored in memory 24 that is substantially similar to the image acquired by the camera element 30. An operator, operating the data acquisition element 22 then compares visually the images already recorded within the database memory 24 with the individual applicant presently standing before the image acquisition element 30. At that time, the operator makes a determination as to whether or not the image of the applicant is already recorded within the database and verifies if a demographic data associated with the matching image corresponds with the demographic data provided by the applicant presently before the operator. If the demographic data matches or sufficiently matches the demographic data provided by the applicant, the operator proceeds to override the enforcement mechanism and allows the existing data record to be updated with the information presently provided by the applicant. Alternatively, if the system operator determines that one or more the images stored within the database substantially represents the applicant presently before the image acquisition element 30, and further that the demographic data provided by the applicant fails to sufficiently to match the demographic data associated with the duplicate images, the system operator stores the applicant's image and new demographic data into an enforcement buffer within the data processor 34 and can have a law enforcement official issue a citation to the applicant.

In a further embodiment of the present invention, the enforcement mechanism couples to the network job builder 18 that generates batch commands that operate the recording unit 14 to manufacture identification cards. In this alternative embodiment, the enforcement mechanism generates a printer control file that lists each data record within the database 24 that includes an image which matches or substantially matches the image of the applicant. The enforcement mechanism prevents the network job builder 18 from generating any batch command that would include a command to generate an identification card for any of these data records. The enforcement mechanism further generates an enforcement list, that lists all data records with matching images. This enforcement list is provided to a law enforcement official for investigation.

Figure 3:
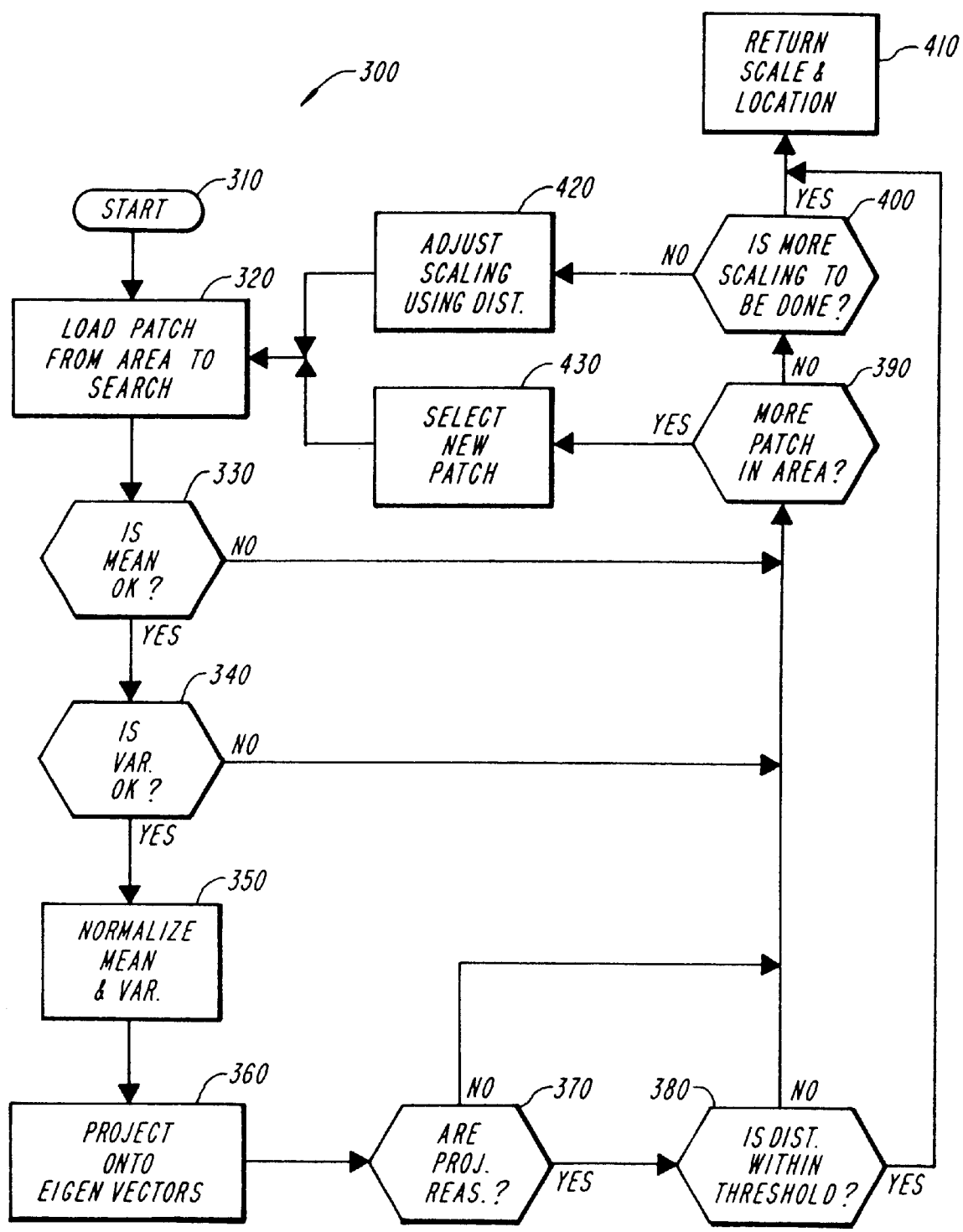
FIG. 3 illustrates a flow chart diagram of a process practicable with the system depicted in FIG. 1, and adapted for finding within a picture an image representative of a face.

In a preferred embodiment of the data acquisition element 22, the verification module includes a lensing module that selects and scales a portion of the acquired image that represents an image of a person's face. FIG. 3 illustrates a flow chart diagram of one process 300 that is implemented by the data processor 34 as a lensing module suitable for practice with the invention.

The process 300, begins with the step 310 when the image acquisition element 30 has acquired an image. In a first step, 320, the process 300 loads a patch of the acquired image into a patch buffer and determines if this patch contains an image of a person's face. An image patch is approximately an 80 pixel by 80 pixel patch of the image captured by the image acquisition element 30. The size of the patch is generally selected to encompass the area of an acquired image, of proper scale, that would include a person's face from approximately the forehead to the lower lip. The process 300 optionally includes a first prefiltering step 330. In step 330, the data processor determines the mean value of the grey scale of the pixel elements that makeup the patch presently loaded into the patch buffer. The data processor 34 compares the mean pixel grey scale value against a user selected grey scale value and determines whether or not the patch loaded into the patch buffer is likely to contain an image of a person's face. In one practice, the mean pixel grey scale value is compared to a reference pixel value that represents the average mean pixel grey scale value for twenty randomly selected images of different faces, i.e. twenty images where each image represents a different face. If, in step 330, the mean pixel grey scale value for the patch in the patch buffer fails to be within a certain range from the reference pixel grey scale value, the process 300 determines that the patch fails to contain an image of a person's face and proceeds to step 390. Typically, the mean pixel grey scale value, prior to normalization, is approximately 76.37. The standard deviation of the mean is typically approximately 27.65. In one practice, if the patch is more that two standard deviations away from the mean value, in either direction, it is rejected for failing to represent a face. It should be obvious to one of ordinary skill that these numbers are empirically determined. Accordingly, different lighting conditions and other factors can effect these values. Alternatively, if the process in step 300 determines that the mean pixel grey scale value is within certain range from the reference pixel grey scale value, the process determines that the image patch in the patch buffer may contain an image of a person's face, and proceeds to step 340.

In step 340 the process 300 includes a further optional prefiltering step wherein the process 300 determines if the pixel grey scale variance, or standard deviation, of the patch loaded into the patch buffer indicates whether the image patch contains an image of a person's face. In one embodiment, the data processor 34, in step 340, determines the pixel variance by the following formula:

$$(VAR-AVGVAR)^2 < THRESHOLD\ (STDDEV\ of\ FACES)^2:$$

where (VAR) represents the pixel variance,(AVGVAR) represents the average variance, (STDDEV of FACES) represents the standard deviation of the pixel grey scale value of a face image, and (THRESHOLD) represents an empirically determined number representative of the average variance of 20 randomly selected images of a face.

If the process 300 determines in step 340 that the variance of the image patch loaded in the patch buffer fails to indicate that the patch contains an image of a face, the process 300 proceeds to step 390 that checks if there are remaining patches in the image that have yet to be tested. Alternatively, if the process step 300 determines that the variance indicates that the image patch in the patch buffer could represent an image of a person's face, the process 300 proceeds to step 350. In step 350 the patch in the patch buffer is normalized with respect to pixel grey scale value to have a normalized mean pixel grey scale value and normalized pixel grey scale variance. In one embodiment, the mean is adjusted to standardized values by finding the current mean. The difference between the existing mean and the desired mean is then added to each pixel value. The standard deviation can be adjusted to a standardized value by computing the current standard deviation. The image is then adjusted on a pixel by pixel basis. In one practice each pixel is adjusted according to the following procedure:

$$pixel=(pixel-mean)*(desired\_std/current\_std)+mean;$$

where pixel is the grey scale pixel value; mean is the mean pixel grey scale value, desired_std is the desired standard deviation and current_std is the current standard deviation. This operation can optionally be performed in multiple iterations.

The process 300 proceeds to step 360 which projects the normalized image patch into the space defined by the reference set of eigenvectors, to generate a set of coefficients that represent a point within the multi-dimensional space defined by the reference set of eigenvectors. The process 300 includes the optional step 370 that analyzes each of the components of the projection signal and determines if each projection is reasonable. In one embodiment of the present invention, the process in step 370 compares each coefficient of the projection signal to an empirically determined reference value that represents the average coefficient value of 20 randomly selected projection signals. In one practice, the data processor 34 in step 370 tests the reasonableness of the projections in the aggregate. Each projection coefficient has its empirical mean subtracted from it. The empirical mean represents an empirically determined value determined from examining the projection signals of a selected set of face images and determining the mean value for the coefficients of these projection signals. An empirical standard deviation can be similarly determined. The difference between the actual and empirical is squared and divided by the variance and added to a variable called the significance. The significance represents a summed value of the deviations of all the coefficients from their means. The significance can, in one embodiment be determined according to:

$$coefficient\_delta=proj[i]-projection\_mean[i]$$

$$significance+=(coefficient\_delta*coefficient\_delta)/(projection\_std[i]*projection\_std[i]);$$

where coefficient_delta represents the difference between the actual coefficient and the empirical mean, proj[i] represents the ith eigenface, projection_mean[i] represents the average coefficient associated with the eigenface i, projection_std represents the standard deviation of the ith eigenface.

The value of the significance for all projections is compared against an empirical threshold. The value of this threshold is dependent on the number of eigenfaces used. In one practice the threshold is set at 25. Accordingly, the generated coefficients are tested to determine if the projection is reasonable, i.e. whether the projection signal can be understood to fall within a user specified range from an empirically determined value that is generated by computing the average coefficient for 20 randomly selected projection signals. If the process 300 determines in step 370 that the projection signals are not reasonable, the process 300 proceeds to step 390 which determines if more image patches are available to test. Alternatively, if the process 300 determines that the coefficients of the projection signal are reasonable, the process 300 proceeds to step 380.

In step 380, the process 300 tests whether the projection signal generated from the image patch in the patch buffer is sufficiently close to the portion of the space defined by the reference eigenvectors and generally indicative of a image representative of a person's face. In one practice, the process 300 determines the distance of the image from face space by reconstructing the face using the eigenfaces and subtracting the resultant reconstruction from the original image, pixel by pixel. The distance signal represents the sum of the differences over the entire image. If step 380 determines that the distance between the point defined by the projection signal and the subspace indicative of an image of a person's face is greater than an empirically determined threshold, the process 300 proceeds to step 390 and determines if more patches are available to examine. Alternatively, if the distance between the projection signal and the subspace is sufficiently close to indicate that the patch in the patch buffer indicates, or represents an image of a face, the process 300 proceeds to step 410 then returns a scale and location factor that represents the scaling factor applied to the acquired image to identify a portion of the image representative of a person's face, and the location within the acquired image, of that portion of the image that represents a person's face. Alternatively, if the process 300 in step 380 determines that the distance is sufficiently large to indicate that the image portion located in the image buffer fails to indicate an image of a person's face, the process 300 proceeds to step 390. In step 390 the process 300 determines if there are remaining portions of the image that have not been tested. If in step 390 the process 300 determines that no more patches are available, the process 300 proceeds to step 400. Alternatively, if the step 390 determines that more patches are available, the process proceeds to step 430.

In one embodiment of the invention, the software lens is adjustable and step 430 selects a new patch according to how close the previous patch was to the face space. The location of the new patch is offset from the previous patch according to a set number of pixels, i.e. an offset. The adjustable software lens selects the offset according to how large the distance signal is. In one practice, the software lens includes a list of offset values, each associated with a range of distances. In step 430, the process selects an offset by identifying which range the distance falls within and selecting the offset associated with that distance. A large distance signal can be associated with a large offset and a small distance signal can be associated with a small offset.

The process 300 in step 390 selects a new patch for testing, and proceeds to step 320 which loads the new patch into the patch buffer. Alternatively, if no more patches are available, the process 300 proceeds to step 400 and tests whether or not the search was successful. In step 400 the process 300 determines if the search was successful by determining if any tested portion of the acquired image indicated the presence of a person's face, as represented by a image patch having a mean and a variance that indicates an image of a person's face within the patch buffer. The process 300 proceeds to step 420 and adjusts the scaling of the image within the patch buffer. In one preferred embodiment of the invention, the data processor 34 adjusts the scaling of the image in the patch buffer as a function of the distance signal generated in step 380. For example, if the distance signal indicates that a projection signal is fairly distant from the portion of space that generally indicates an image of a person's face, the process 300 in step 420 significantly adjusts the scaling factor of the image patch. Alternatively, if the distant signal is relatively small, the data processor makes a minor adjustment to the scaling factor. In one practice the scaling factor is selected from a set of empirically determined values, where each value is associated with a range of distances. Accordingly, the scale factor is selected by examining the distance signal and selecting the scale factor associated with that range.

Once the process 300 adjusts the scaling factor, the process proceeds to step 320 and starts all over by loading the first patch back into the image buffer and testing this patch having rescaled the image.

In a further alternative embodiment, the process 300 is adapted to identify a select portion of an image of a person's face, such as the eyes, the nose or the mouth. In this embodiment, the process searches an image to identify those portions of an image representative of the selected facial feature. In this alternative process, the mean pixel value of the image patch loaded into the image buffer is compared to a reference mean that represents an empirically determined standard mean pixel grey scale value for the portion of an image that contains the selected facial feature, such as an image of a person's eyes. Similarly, the variance of the image patch is tested against a reference variance that represents the variance of the portion of an image that contains the selected feature. Further, this alternative practice projects the image patch onto a set of reference eigenvectors wherein each reference eigenvector is adjusted to represent a vector in a space computed by reference to a plurality of reference images each which image represents the selected facial feature. In practice, this alternative process allows the verification module to compare select facial features of different images. Accordingly, a system operator can employ this alternative practice to detect images recorded in the database memory 24 that have select facial features which are similar to the facial features of the applicant standing in front of the image acquisition element 30. Consequently, the verification module can circumvent the use of disguises by an applicant attempting to fraudulently obtain registration into the database stored in memory 24.

In a further preferred embodiment of the present invention, the data processor 34 receives the scale factor and location from the verification module, and stores these values, or signals representative of these values, within the image file that contains the image, or signals representative of the acquired image, for employment by the recording unit 14. In particular, the recording unit 14 accesses an image file within the image database memory 36, and records onto a datacard 40 an image representative of the person's face. The recording unit 14 is preferably adapted to include a processing unit that accesses the image file stored in the image database memory 24 to collect both the image information and the scaling factor and location information. The recording unit 14 employs the scaling factor information and location information to record the image information in a uniform format onto the datacard 40. In particular, the recording unit 14 employs the scaling factor to record the image of the person's face with a selected scale, i.e. a selected size. Furthermore, the recording unit 14 employs the location information to identify the center of the image of a person's face. The recording unit 14 disposes the center of a person's face at a particular location within the image recorded onto the datacard 40. Accordingly, the recording unit 14 employs the scaling factor and the location information to generate a more uniform recorded image, whereby images recorded onto datacards 40 are of uniform scale and uniform position. Alternatively, the scaling factor and location information are provided to the image server 20 or the network job builder 18, which can adjust the image before transmitting the image to the recording unit 14. This uniformity of images increases the difficulty of creating a forged identification card by making it more difficult to manufacture an identification card that has the same characteristics as an identification card manufactured by the authorized system 10.

In another preferred embodiment of the invention, the data processor 34 includes a sorting module that employs the verification module to search and sort images within the image database memory 24, to identify those images stored within the image database 24 that fail to represent or include an image of a person's face. In one embodiment, the system 10 employs the sorting module to sort a database of images that were loaded into an image database 24. For example, the system 10 employs the sorting module to perform an initial search and sort on a set of images that are loaded into the image database memory 24 from an acquisition element that does not include an element for verifying that an image contains or represents a person's face. In operation, the sorting module selects each image file stored within the image database memory 24 and, as discussed above with reference to FIG. 3, loads an image patch from the image into a patch buffer. The verification module examines the loaded image patch to determine if this image patch contains an image representative of a person's face. The sorting module proceeds to inspect each image file stored within the image database memory 24 and generates a list of those image files that fail to contain an image of a person's face. The list is provided to a system operator who accesses each image file and displays the image onto the monitor 32. The system operator verifies whether or not the image file contains an image representative of a person's face. Each image file that fails to contain an image of persons' face is recorded in a list, and the list is passed to a law enforcement official to determine if a person has been fraudulently obtaining benefits under this data record. Accordingly, the sorting module enables the system 10 to identify those records within an official record that have been fraudulently entered into an official record.

Once the data acquisition element has determined that a data record is to be entered into the official database, the recording unit 14, vision inspection 12 and packaging unit 16 operate to generate an identification card that records, typically in a printed format, the information, or portions of the information, stored in a data record. Generally, the vision inspection cell 12, recording unit 14, and packaging unit 16 operate under the control of the network job builder 18 to generate batch commands, that represent a series of print commands, wherein each print command corresponds to a command to generate an identification card that records onto that card information from one data record.

To this end, the vision inspection cell 12 connects via an RS244 port to the network job builder 18. The vision inspection cell 12 includes a central processing unit 26, a collection unit 28, a support fixture 42, a camera element 44, a cell lighting unit 46, a barcode reader 48, and an image buffer memory 49. The recording unit 14 includes a central processing unit 50, a data memory 52, a card source 54, a recorder unit 56, a barcode decoding unit 58 and an input hopper 60. The packaging unit 16 includes an output hopper 62, a central processing unit 64, a magnetic stripe encoder/decoder unit 66, a printer 68 and a packaging assembly unit 70. In an alternative embodiment of the invention, the packaging assembly unit 70 can further include an envelope sealer and a postage metering device.

As depicted in FIG. 1, the network job builder unit 18 connects via a transmission path to the central processing unit 50 of the printing unit 14. In a preferred embodiment of the present invention the transmission path is an RS244 serial communication port, and the network job builder unit 18 and the central processing unit 50 contain RS244 serial interface units. Such interface units are of the type commonly used in small computer communications and any of the conventional RS244 communication units can be practiced with the present invention.

As previously described, the network job builder 18 can include a processing unit 18A, a program memory 18B and a data memory 18C of the type commonly used by data processing devices. The processing unit 18A connects to the data memory 18C and the program memory 18B, and operates according to a set of program instructions stored in the memory 18B to generate a manufacturing batch file that includes a command field and data field. The command field includes signals that actuate the recording unit 14 to record on documents, such as the blank cards 40 located in the card source 54, the one or more data records stored in the data field.

The recording unit 14 illustrated in FIG. 1 is a document manufacture machine of the type suitable for printing in black and white, or in color. The illustrated recording unit 14 records data on one or both sides of the document, such as a 2×3½ in. plastic card, and can record image data, text data and graphic data. In the depicted embodiment the CPU 50 reads the manufacturing batch files generated by the network job builder 18 and generates command signals for the recording unit 56, to record text graphic and image data onto a blank card 40. The recorder 56 includes a mechanical linkage for collecting a blank card 40 from a card source 54 and for moving the card 40 through the recorder 56. The mechanical linkage assembly (not shown) can include sets of rollers having textured exterior surfaces suitable for frictionally engaging a plastic card. The rollers contact the cards 40 in card source 54 and extract the cards 40 one at a time. The mechanical linkage assembly moves each card 40 through the linkage assembly with pairs of rollers radially spaced from each other and connected to motor assemblies that rotate the rollers in opposing directions. The rotating rollers feeds the cards 40 one at a time through the recording unit 14.

As cards 40 move through the recording unit 14, the recorder 56 records text, graphic, image data or combinations thereof onto the card 40. The data recorded onto each card 40 corresponds to a data record stored in the data memory 52. The data record includes an identification signal that distinguishes one record from the next. The data record stored in the data memory 52 is typically part of the manufacturing batch file transmitted from the network job builder 18. The CPU 50 controls the recorder unit 56 to select one blank card 40 for each data record stored in the data memory 52. The CPU 50 can control the recorder 56 to record the text, graphic and image data of one data record onto one card 40 moving through the recorder unit 56. The recorder 56 can, therefore, receive one blank card 40 and one data record to generate a data card 90 having data from that data record recorded thereon.

The illustrated recorder 56 includes the barcode unit 58. The barcode unit 58 has a mechanical linkage assembly for collecting each data card 90 having recorded data and includes a barcode printer for recording onto each data card 90 a barcode identification graphic that corresponds to the identification signal field in the associated data record. In one embodiment of the present invention the barcode unit 58 records onto the selected data card 90 a barcode graphic representative of the driver's license number. The recorded driver's license number is one identification signal that can uniquely identify each data card 90 being manufactured by the recording unit 14 and the system 10. In other embodiments and practices of the present invention, the barcode unit 58 has a mechanical linkage that connects to the input hopper 60 and that stores completed data cards 90 in the input hopper 60. The recording unit 14 can be a data card manufacturing unit of the type conventionally used for producing plastic identification cards. One such type is the data card 9000 plastic manufacture machine, sold by the Data Card Corporation in Minnetonka, Minn.

In the illustrated embodiment, a collection unit 28 in the vision inspection cell 12 collects data cards 90 from the input hopper 60. The collection unit 28 in the illustrated embodiment is a robotic arm having a robotic end effector with a vacuum cup grip 29 adapted for removing the data card 90 from the input hopper 60. The robotic arm collection unit 28 collects a data card 90 from the input hopper 60 and moves the data card 90 in front of the barcode reader 48. The illustrated barcode reader 48 has a laser scanning unit for reading a barcode recorded on one side of the data card 90. The barcode reader 48 includes a processing unit for decoding a barcode graphic recorded onto the data card 90. The decoded barcode signal representing the decoded information is transmitted to the CPU 26 and stored in a data memory of the CPU 26. The CPU 26 can use the barcode information to identify the data record in the manufacturing batch file, which is associated with the data card 90 held by the robot arm collection unit 28. In one embodiment, the CPU 26 transmits via the serial interface, a data record request to the network job builder 18 for the data record associated with the decoded identification signal. The processing unit 18A of the network job builder 18 decodes the data record request and retrieves the corresponding data record from a manufacturing batch file stored in the data memory 18B, and transmits the data record to the CPU 26 via the RS-244C interface.

The vision inspection cell 12 compares the information in the data record against the information recorded on the associated data card 90.

The depicted robot arm collection unit 28 is a TT8010 robotic arm manufactured by the Seiko Instruments Corporation. The robotic arm is equipped with a vacuum cup end effector adapted for gripping data cards 90. The vacuum can be generated by a vacuum pump such as the Fast Vac TT No. VP61-GOH and creates a vacuum sufficient to hold the card 90. The illustrated cup 29 includes a vacuum feedback sensor to detect the presence of a data card 90 at the end effector. The detection of a vacuum at the end effector indicates that a data card 90 is gripped against the end effector. The failure to detect a vacuum indicates that a data card 90 is not present against the cup 29. The vacuum assembly couples via a transmission path to the CPU 26. The CPU 26 monitors the vacuum sensor and the sensor element 72 to determine from the position of the collection unit 28 and the presence of a data card 90 at the cup 29, whether the collection unit 28 is properly moving the data card 90 through the system 10.

With reference again to FIG. 1, the illustrated support fixture 42 has a sensor 74 that connects to the support fixture 42 for being able to detect when a data card 90 has been inserted therein. The sensor 74 connects via a transmission path to the CPU 26. The CPU 26 can detect the presence of a data card 90 within the support fixture 42 and activate the camera element 44 to begin the inspection process.

In one embodiment of the present invention the camera unit 44 consists of four camera units. Two camera units are arranged with the support fixture 42 for taking images of the front side of the data card 90. The two other cameras are arranged with the support fixture 42 for taking images of the rear portion of the data card 90. Each set of paired cameras is arranged for taking an image of the left or right portion of one side of the data card 90. As depicted in FIG. 1, the camera unit 44 connects via a transmission path through CPU 26. The CPU 26 can actuate the camera unit 46 by transmitting a control signal via the transmission path to the camera unit 44. In one embodiment of the present invention, the CPU 26 acquires images of the data card 90 in the fixture 42 by acquiring four images of the card, a front left image, a front right image, a back left image, and a back right image. The image data generated by the camera unit 44 is transmitted via the transmission path to the CPU 26. The program sequence operating the CPU 26 generates, for each image acquired from the data card 90, a data file. The data file stores an image signal representative of the image captured by each camera in the camera unit 44. Each data file is stored in the data memory of CPU 26. The CPU 26, further includes an image memory buffer 49. The program sequence operating the CPU 26, stores in the image memory buffer 49, a copy of the image signal transmitted from the network job builder unit 18 for the respective card being manufactured. The CPU 26, generates a comparison signal by comparing the image data acquired from the data card 90 in the fixture 42 with the image data used to manufacture the data card 90 in the recording unit 14 to manufacture the data card 90. In one preferred embodiment of the invention, the CPU 26 generates a projection signal from the image data that represents the image of a person's face and compares the generated projection signal with a component signal stored in the image file. If the signals are substantially identical, the CPU 26 generates a signal that verifies that the image has been recorded correctly, and that the recorded image matches the image of the data record. Alternatively, the CPU 26 generates an image recording error signal indicating that the datacard has an error. The comparison signal is transmitted via the transmission path to the network job builder 18 and stored in a status file that can be transmitted to the control image server 20 as a status report.

As will be described in greater detail hereinafter, the comparison signal includes a status signal that represents the status of the document. The status signal indicates whether the document being inspected has passed or failed the inspection. In one embodiment of the present invention, if a document fails inspection three times, the system 10 declares the document is failed to manufacture and this failure status is sent via the network job builder 18 to the central image server 20. Alternatively, the vision inspection cell 12 can generate a comparison signal having a status signal that indicates that the document is within tolerance. The vision inspection cell 12 can send a document successfully manufactured status signal back to the network job builder 18 and to the control image server 20. Further the vision inspection cell 12 can transmit the magnetic stripe and addressing record for the respective document such as a data card 90, to the packaging unit 16. If the document such as the data card 90, is not within tolerance and the vision inspection cell 12 generates a status signal indicating a failed to manufacture document, the vision inspection cell 12 transmits an invalid magnetic stripe and addressing record to the packaging unit 16. The invalid magnetic stripe and addressing record causes the document to fail the magnetic stripe verification pass within the packaging unit 16 and the document is rejected and placed within a reject bin 76.

The illustrated packaging unit 16 is mechanically connected to the vision inspection cell 12 by the output hopper 62 and is electronically coupled to the vision inspection cell 12 by the transmission path that connects CPU 64 with the CPU 26. The packaging unit includes a unit 66, such as the illustrated magnetic stripe reader unit 66, that can decode an identification signal, such as a social security number, recorded onto the data card 90. The illustrated packaging unit 16 receives a data card 90 through the output hopper 62 and receives data record files via the transmission path coupling CPU 64 to CPU 26. The CPU 64 detects the presence of documents in the output hopper 62 by a sensor mechanism located within the output hopper 62. The CPU 64 can activate a mechanical linkage assembly of the type previously described to remove a data card 90 from the output hopper 62 and to insert the card 90 into a magnetic stripe unit 66. CPU 64 further collects from the CPU 26 the data record paired with the document in the magnetic stripe unit 66. In the illustrated embodiment, the CPU 26 reads the data record from the CPU 50 via the serial interface transmission path and store the data record in the data memory within the CPU 64. Alternative data transfer systems for collecting the data record associated with the identification signal read by the packaging unit 16 can be practiced with the present invention without departing from the scope thereof. The illustrated magnetic stripe unit 66 reads the magnetic stripe on the back of the data card and transmits the magnetic stripe information to the CPU 64. The CPU 64 compares the data encoded on the magnetic stripe with the data in the data record file to verify that the magnetic stripe has been encoded correctly and to verify that the data card in the magnetic stripe unit 66 corresponds to the data file stored in the data memory of CPU 64. If the CPU 64 detects that the magnetic stripe has been correctly encoded with the information from the data record and the data memory, a mechanical linkage removes the card from the magnetic stripe unit 66 to the package assembling unit 70.

The CPU 64 transmits via a transmission path, data from the document file associated with the respective card to the printer unit 68. The printer unit 68 addresses a document carrier with the information from the data file. In one embodiment of the invention CPU 64 transmits one field of information to the printer unit 68, typically this field of information is the address record for the data card being manufactured. The printer unit 68 records the address data onto a document carrier. The document carrier is transferred via mechanical assembly to the package assembly 70 that places the data card 90 into the document carrier. A mechanical assembly collects the document carrier and places the document carrier with the enclosed data card 90 into the carrier bin 78.

Alternatively, the packaging unit 16 rejects data card 90 having information misrecorded thereon. In a first practice, the CPU 64 compares the magnetic stripe data read by magnetic stripe unit 66 with data from the data file in the CPU 64 memory. CPU 64 detects errors in the recorded magnetic stripe data and transfers the data card 90 and the magnetic stripe unit 66 via a mechanical assembly to the reject bin 76.

In a preferred practice of the invention, CPU 64 rejects data card 90 to remove from the system 10 those data cards that fail visual inspection within the vision inspection cell 12. In one embodiment, the CPU 26 and vision inspection cell 12 detect an error during the visual inspection of a data card 90. The collection unit 28 places the data card 90 into the output hopper 62 and the CPU 26 alters the data field for the respective data card to include a blank signal in the data field. The CPU 26 transfers the data field with the blank signal to the CPU 64 when the corresponding data card 90 is selected from the output hopper 62 and then placed in the magnetic stripe unit 66. The CPU 64 compares the information encoded on the magnetic stripe with the blank signal detects the mismatch and activates the mechanical assembly to remove the data card from the magnetic stripe unit 66 and place the data card into the reject bin 76. In this way, data cards 90 that fail inspection are sorted out of the successfully manufactured cards by the packaging unit 16.

The above description of certain illustrated embodiments is not intended to limit the scope of the present invention, or to represent all configurations, practices, or realizations of the present invention. Furthermore, it should be apparent to one of ordinary skill in the art of electrical engineering that certain modifications can be made to the present invention, without departing from the scope thereof. Accordingly, the scope of the present invention is to be determined with reference to the following:

We claim:

1. In a system for generating identification cards having an image acquisition element for acquiring an image of a face of a selected person requesting an identification card, a computer system comprising:

a database having data regarding registered persons having a previously manufactured identification card, wherein the database holds for each of the registered persons, personal information and a representation of an image of a face of the registered person, said representation comprising a weighted set of eigenvector values for a multi-dimensional image space that are associated with the face of the registered person;

a recognition component for searching the database and recognizing a substantial match between the image of the face of the selected person acquired by the image acquisition element and one of the representations of an image of a face of a given registered person in the database;

a comparison component for determining if personal information provided by the selected person matches personal information of the given registered person when the comparison component recognizes a substantial match between the image of the face of the selected person acquired by the image acquisition element and the representation of the image of the face of the given registered person in the database; and an enforcement component for preventing generation of an identification card for the selected party where the recognition component recognizes a substantial match and the comparison component determines that the personal information provided by the selected person does not match personal information of the given registered person in the database.

2. The system of claim 1 wherein the enforcement mechanism includes an element for buffering the image acquired by the image acquisition element in a buffer when the enforcement component prevents generation of an identification card.

3. The system of claim 2 wherein the element for buffering also buffers the personal information provided by the selected person in the buffer.

4. The system of claim 1 wherein the enforcement mechanism includes an element for identifying and preserving in a data structure personal information of the given registered person from the database when the enforcement component prevents generation of an identification card for the selected party.

5. In an apparatus for generating identification cards having an image acquisition element and a computer system, a method comprising the computer implemented steps of:

receiving an image of a face of a selected person requesting an identification card from the image acquisition element;

providing a database having data regarding registered persons having a previously manufactured identification card, wherein, for each of the registered persons, the database holds personal information and a representation of an image of a face of the registered person comprising a weighted set of eigenvector values, for a multi-dimensional image space, that are associated with the face of the registered person;

searching the representations of images of faces of registered persons in the database;

recognizing a substantial match between the image of the face of the selected person acquired by the image acquisition element and one of the representations of an image of a face of a given registered person in the database;

where a substantial match is recognized, determining if personal information provided by the selected person matches personal information of the given registered person in the database;

preventing an identification card for the selected party from being generated, where a substantial match is recognized and it is determined that the personal information provided by the selected person does not match personal information of the given registered person in the database.

6. The method of claim 5 wherein the method further comprises buffering the image acquired by the image acquisition element in a buffer when the generation of an identification card for the selected party is prevented.

7. The method of claim 6 wherein the method further comprises buffering the personal information provided by the selected person in the buffer.

8. The method of claim 5 wherein the method further comprises identifying and preserving personal information of the given registered person from the database in a data structure when generation of an identification card for the selected party is prevented.

9. In an apparatus for generating identification cards having an image acquisition element and a computer system with a database having data regarding registered persons possessing identification cards, wherein, for each of the registered persons, the database holds personal information and a representation of an image of a face of the registered person comprising a weighted set of eigenvector values, for a multi-dimensional image space, that are associated with the face of the registered person, a computer-readable medium holding computer-executable instructions for performing a method comprising the computer implemented steps of:

receiving an image of a face of a selected person requesting an identification card from the image acquisition element;

searching the database;

recognizing a substantial match between the image of the face of the selected person acquired by the image acquisition element and one of the representations of an image of a face of a given registered person in the database;

where a substantial match is recognized, determining if personal information provided by the selected person matches personal information of the given registered person in the database;

preventing an identification card for the selected party from being generated, where a substantial match is recognized and it is determined that the personal information provided by the selected person does not match personal information of the given registered person in the database.

10. The computer-readable medium of claim 9 wherein the method further comprises buffering the image acquired by the image acquisition element in a buffer when the generation of an identification card for the selected party is prevented.

11. The computer-readable medium of claim 10 wherein the method further comprises buffering the personal information provided by the selected person in the buffer.

12. The computer-readable medium of claim 9 wherein the method further comprises identifying and preserving personal information of the given registered person from the database in a data structure when generation of an identification card for the selected party is prevented.

* * * * *